United States Patent [19]

Furman et al.

[11] Patent Number: 5,266,560
[45] Date of Patent: Nov. 30, 1993

[54] PHARMACEUTICAL INSULIN-POTENTIATING CR(III) COMPLEXES WITH GTF-LIKE ACTIVITY

[75] Inventors: Sydney C. Furman, Union City; Charles T. Goetschel, Walnut Creek; Branko Huc, Palo Alto; Thomas H. Nufert, Hayward, all of Calif.

[73] Assignee: Thomas Research Corporation, Concord, Calif.

[21] Appl. No.: 756,531

[22] Filed: Sep. 9, 1991

Related U.S. Application Data

[60] Division of Ser. No. 666,993, Mar. 11, 1991, abandoned, which is a continuation of Ser. No. 202,965, Jun. 3, 1988, abandoned.

[51] Int. Cl.$^5$ .................. A61K 31/555; C07D 213/89
[52] U.S. Cl. ........................................ 514/4; 514/492; 514/866; 514/188; 546/5
[58] Field of Search ............... 514/4, 492, 866, 188; 546/5

[56] References Cited

U.S. PATENT DOCUMENTS

| | | | |
|---|---|---|---|
| 4,343,905 | 8/1982 | Szalay | 424/195.1 |
| 4,921,877 | 5/1990 | Cashmere et al. | 514/904 |
| 4,923,855 | 5/1990 | Jensen | 514/188 |
| 4,954,492 | 9/1990 | Jensen | 514/188 |
| 4,985,439 | 1/1991 | Hwang et al. | 514/188 |

*Primary Examiner*—Ronald W. Griffin
*Attorney, Agent, or Firm*—Fliesler, Dubb, Meyer & Lovejoy

[57] ABSTRACT

A composition of matter having GTF-like activity, its preparation and its use in treating chromium deficiency and insulin resistance diseases such as diabetes are set forth. The composition comprises:

(Formula 1)

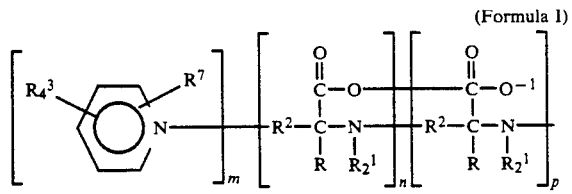

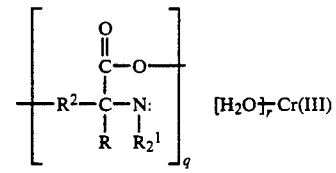

$m = 1, 2$ or $3$; $n = 0, 1$ or $2$; $p = 0, 1, 2, 3, 4$ or $5$;
$q = 0, 1, 2, 3, 4$ or $5$; $r = 0, 1, 2$ or $3$;
$m + 2n + p + q + r \leq 6$;
if p and q both $= 0$, $n = 1$ pr z;
if $n = 0$, p and/or $q \neq 0$;
including mixtures and oligomers thereof, wherein:

each $R^1$ is independently selected from hydrogen, $C_{1-3}$ alkyl, $C_{2-3}$ alkenyl and $C_{2-3}$ alkynyl, or two $R^1$ form a ring having, including the N atom to which they are attached, 5 to 7 ring atoms;

each $R^2$ is independently selected from hydrogen, $C_{1-4}$ alkyl, $C_{2-4}$ alkenyl and $C_{2-4}$ alkynyl or two adjacent $R^1$ and $R^2$ form a ring having, including the N and C atoms to which they are attached, 5 to 7 ring atoms;

each $R^3$ is independently selected from hydrogen, fluoro, chloro, bromo, $C_{1-4}$ alkyl, $C_{2-4}$ alkenyl, $C_{2-4}$ alkynyl, COOH, COOR$^6$, CHO or COR$^6$, wherein R$^6$ is selected from $C_{1-4}$ alkyl, $C_{2-4}$ alkenyl and $C_{2-4}$ alkynyl or two adjacent $R^3$ from a ring having, including the atoms of the aromatic nitrogen containing ring to which they are attached, 5 to 7 ring atoms;

$R^7$ is CN or $CR_2^8OH$, $CR_2^8SH$, or $CR_2^8NH_2$, wherein each $R^8$ is independently H, $C_{1-4}$ alkyl, $C_{2-4}$ alkenyl or $C_{2-4}$ alkynyl, or COX, CSX or CNHX, wherein each X is independently H, $C_{1-4}$ alkyl, $C_{2-4}$ alkenyl, $C_{2-4}$ alkynyl, OY, $NR_2^4$ or SY, wherein Y is hydrogen, alkyl, an alkali metal or ammonium ion and each $R^4$ is independently selected from hydrogen, $C_{1-4}$ alkyl, $C_{2-4}$ alkenyl or $C_{2-4}$ alkynyl, or two geminal $R^4$ form a ring having, including the nitrogen atom to which they are attached, 5-7 ring atoms;

and each R is independently selected such that $R_2^1NCRR^2COOH$ is an amino acid or a peptide having no more than 6 amino acid residues, optionally having one or more of the substituents SH, $NH_2$, OH, COOH, $CH_2OH$, $OCH_3$, $OC_2H_5$, $SCH_3$, $SC_2H_5$, NH, Cl, Br, F, CCH or CN.

10 Claims, No Drawings

PHARMACEUTICAL INSULIN-POTENTIATING CR(III) COMPLEXES WITH GTF-LIKE ACTIVITY

This application is a divisional of Ser. No. 07/666,993, filed Mar. 11, 1991, now abandoned, which is a continuation of Ser. No. 07/202,965, filed Jun. 3, 1988, now abandoned.

FIELD OF INVENTION

The invention relates to a pharmaceutical composition of matter, its method of manufacture, and its therapeutic use. More particularly, the invention relates to a composition of matter having GTF-like activity (see Mertz, W., Physiological Reviews, 49, 163, 1969 for a discussion of "Glucose Tolerance Factor" (GTF) in that it is useful in the treatment of diseases and disorders involving insulin resistance such as non-insulin dependent diabetes mellitus. The invention also provides a form of readily absorbable chromium for dietary chromium supplementation for replenishing low body stores of chromium.

BACKGROUND OF THE INVENTION

Levels of chromium in the U.S. diet may be less than optimal for certain individuals and marginal deficiency states may exist particularly in pregnancy and old age (*Recommended Dietary Allowances*, 9th edition, National Academy of Sciences). Chromium compounds which are physiologically available, safe and stable would be useful to enrich and fortify foods, or for use as a dietary supplement.

Diabetes is an ongoing problem which has only been partially controlled by the use of insulin therapy and dietary adjustments. There are two principal forms of diabetes. Diabetics who suffer from insulin-dependent-diabetes mellitus (IDDM) fail to produce adequate amounts of insulin. IDDM diabetics comprise about 10% of the total population of diabetics. Non-insulin-dependent-diabetes mellitus (NIDDM) diabetics do produce insulin, often 2-3 times normal amounts, but fail to adequately utilize insulin. This failure in utilizing the body's own insulin is termed insulin resistance. Roughly 90% of all diabetics have insulin resistance. It is recognized that insulin resistance and an attendant hyperinsulinemia are associated with a host of diseases including obesity, hypertension, coronary artery disease, hyperlipidemia and Cushing's syndrome as well as NIDDM diabetes.

Compounds which significantly potentiate (compounds which reduce insulin resistance and thereby augment insulin action are referred to herein as "potentiators") insulin action, at times referred to herein as having GTF-like activity, if available, would be useful in treating insulin resistance and would be potentially useful in treating insulin resistance diseases depending upon the degree which insulin resistance contributes to the overall pathophysiology. Such compounds would, if available, be useful in the treatment of IDDM diabetics who are also insulin resistant. The amount of supplemental insulin normally prescribed for such diabetics could be significantly reduced.

It has been known for some time that extracts of yeast and other natural products include GTF which is a compound or mixture of compounds, along with impurities. GTF has been postulated to be an effective factor in aiding NIDDM diabetics. Its precise structure, or even whether it is one compound or a mixture of compounds, is the subject of conjecture but is not known. Workers in the field have developed data which indicate that GTF includes one or more nicotinic acid moieties, chromium, and certain amino acids (glutamic acid, cysteine and glycine) corresponding to those in glutathione; Toepfer, Z. W., J. Agric. Food Chem. 25, No. 1, 162–66 (1977). From these partial data it has been postulated by Mertz that glutathione may be one of the moieties forming GTF. Pure, or even nearly pure, GTF has not previously been synthesized and its exact structure is not known.

Over the years a number of attempts have been made to synthesize GTF and a number of compounds having at least some GTF-like activity have been reported. Indeed, some of the compounds reported in the literature have been incorrectly postulated as probably containing two nitrogen-bound nicotinic acid moieties per one chromium atom. Such results are presented, for example, by Anderson, et al, J. Agric. Food Chem. Vol. 26, No. 5, 1978 at pages 1219–1221. Anderson, et al also mention a chromium-nicotinic acid-glutathione material as having GTF-like activity in Federation Proceedings 36, 1977, as reported on page 11 in Abstract No. 4507. Polyhedron Report No. 9, Polyhedron Vol. 4, No. 1, pages 1–14, 1985, discusses the Anderson, et al result on pages 3–5. And, a number of postulated but unproven structures for GTF appear later in this article. Also, in Trace Element Metabolism in Man and Animals-3, Proceedings of the 3rd International Symposium, Freising, Fed. Rep. of Germany, July 1977, particularly on page 272 thereof, in an article by Mertz, et al, a discussion of a possible structure of GTF is set forth. Still further, in Chromium in Nutrition and Disease, G. Saner, Alan R. Liss, Inc., Publisher, New York, N.Y., 1980, particularly on page 9 thereof, a discussion is set forth relating to tetra-aquo-di-nicotinato chromium complexes.

The prior art attempts to synthesize GTF and GTF-like compounds have been concerned with reacting Cr(III) salts with such materials as nicotinic acid and glutathione (or select amino acids). As a result, the prior art, as is shown experimentally below, has not succeeded in forming Cr(III), nicotinic acid, glutathione (or amino acid) compounds wherein the Cr(III) has been attached to the nicotinic acid moiety via the nitrogen in the aromatic nitrogen containing (pyridine) ring.

With all of the above theories and all of the prior attempts to synthesize GTF and GTF-like compounds, none of the synthesized compounds has the effectiveness of, nor the structure of, GTF itself. The synthesis of GTF, or of compounds having comparable GTF-like activity to GTF, would be very beneficial in that such compounds could then be produced in quantity and be utilized to treat insulin resistance-related disorders.

It has been observed (Doisy, et al, *Excerpta Medica*, Int. Cong. Series, 280, 155 Abstracts, 1973) that injecting db/db mice with yeast extracts containing high GTF can delay the spontaneous degeneration of the insulin-producing beta cells of the pancreas. Therefore, there may also be a use of GTF-like compounds for treating IDDM diabetes.

The present invention is directed to overcoming one or more of the problems as set forth above.

DISCLOSURE OF INVENTION

In accordance with one embodiment of the present invention a composition of matter is set forth having GTF-like activity. The composition of matter comprises

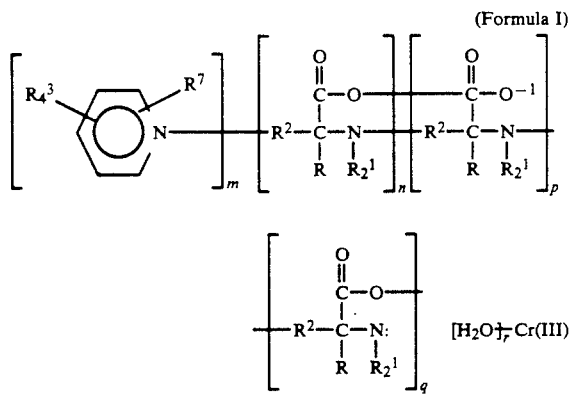

(Formula I)

$$\left[R_4^3 \underset{N}{\bigotimes} R^7\right]_m \left[\underset{R}{\underset{|}{R^2}} - \overset{O}{\underset{R_2^1}{\overset{||}{C}}} - \overset{O}{\underset{|}{N}} \right]_n \left[\underset{R}{\underset{|}{R^2}} - \overset{O}{\underset{R_2^1}{\overset{||}{C}}} - \overset{O}{\underset{|}{N}} - O^{-1}\right]_p$$

$$\left[\underset{R}{\underset{|}{R^2}} - \overset{O}{\underset{R_2^1}{\overset{||}{C}}} - \overset{O}{\underset{|}{N:}} \right]_q \quad [H_2O]_r \; Cr(III)$$

m=1, 2 or 3; n=0, 1 or 2; p=0, 1, 2, 3, 4 or 5;
q=0, 1, 2, 3, 4 or 5; r=0, 1, 2 or 3;
m+2n+p+q+r≧6;
if p and q both=0, n=1 or 2;
if n=0, p and/or q≠0;
including mixtures and oligomers thereof, wherein:
  each $R^1$ is independently selected from hydrogen, $C_{1-3}$ alkyl, $C_{2-3}$ alkenyl and $C_{2-3}$ alkynyl, or two $R^1$ form a ring having, including the N atom to which they are attached, 5 to 7 ring atoms;
  each $R^2$ is independently selected from hydrogen, $C_{1-4}$ alkyl, $C_{2-4}$ alkenyl and $C_{2-4}$ alkynyl or two adjacent $R^1$ and $R^2$ form a ring having, including the N and C atoms to which they are attached, 5 to 7 ring atoms;
  each $R^3$ is independently selected from hydrogen, fluoro, chloro, bromo, $C_{1-4}$ alkyl, $C_{2-4}$ alkenyl, $C_{2-4}$ alkynyl, COOH, COOR$^6$ CHO or COR$^6$, wherein $R^6$ is selected from $C_{1-4}$ alkyl, $C_{2-4}$ alkenyl and $C_{2-4}$ alkynyl or two adjacent $R^3$ form a ring having, including the atoms of the aromatic nitrogen containing ring to which they are attached, 5 to 7 ring atoms;
  $R^7$ is CN or $CR_2^8OH$, $CR_2^8SH$, or $CR_2^8NH_2$, wherein each $R^8$ is independently H, $C_{1-4}$ alkyl, $C_{2-4}$ alkenyl or $C_{2-4}$ alkynyl, or COX, CSX or CNHX, wherein each X is independently H, $C_{1-4}$ alkyl, $C_{2-4}$ alkenyl, $C_{2-4}$ alkynyl, OY, $NR_2^4$ or SY, wherein Y is hydrogen, alkyl, an alkali metal or ammonium ion and each $R^4$ is independently selected from hydrogen, $C_{1-4}$ alkyl, $C_{2-4}$ alkenyl or $C_{2-4}$ alkynyl, or two geminal $R^4$ form a ring having, including the nitrogen atom to which they are attached, 5-7 ring atoms;
  and each R is independently selected such that $R_2^1NCRR^2COOH$ is an amino acid or a peptide having no more than 6 amino acid residues, optionally having one or more of the substituents SH, NH$_2$, OH, COOH, CH$_2$OH, OCH$_3$, OC$_2$H$_5$, SCH$_3$, SC$_2$H$_5$, NH, Cl, Br, F, CCH or CN.

In accordance with another embodiment of the present invention a method is set forth of synthesizing a composition of matter as set forth above. The method comprises mixing together in a reaction chamber under a non-oxidizing atmosphere, a Cr(II) solution and a solution of CRR$^2$(NR$_2^1$)COOH, where R, R$^1$ and R$^2$ are as previously defined, to form a first reaction mixture. The first reaction mixture is maintained at a pH of about 4 to about 7 for a period of time sufficient for the Cr(II) and CRR$^2$(NR$^1$H)COOH to react and form a first compound. A compound having the formula

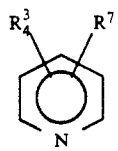

wherein $R^7$ is in the 2-, 3-, or 4-ring position, is added to the reacted first reaction mixture under a non-oxidizing atmosphere to form a second reaction mixture wherein $R^7$ and $R^4$ are as defined previously. The second reaction mixture is held under a non-oxidizing atmosphere for a time sufficient for the

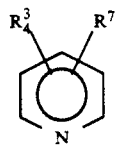

to react with the first compound and form the composition of matter set forth above.

In accordance with still another embodiment of the present invention a method is set forth for synthesizing a composition of matter as set forth above. The method comprises mixing together in a reaction chamber under a non-oxidizing atmosphere a Cr(II) solution and a compound having the formula

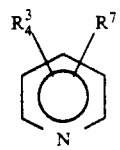

wherein $R^3$ and $R^7$ are as previously defined to form a first reaction mixture. A solution of CRR$^2$(NR$_2^1$)COOH, wherein R, R$^1$ and R$^2$ are as previously defined, is added to the first reaction mixture. The first reaction mixture is maintained at a pH of about 4 to about 7 for a period of time sufficient for a composition of matter as set forth above to form.

In accordance with yet another embodiment of the invention the three components are combined and maintained at a pH of about 4 to about 7 for a period of time sufficient for the composition of matter as set forth above to form.

In accordance with another embodiment still of the present invention methods are set forth of treating chromium deficiency and insulin resistance diseases. The methods comprise administering a pharmacologically effective amount of the composition of matter set forth above to a chromium deficient or an insulin resistant individual.

The composition of matter set forth above has high GTF-like activity and may, indeed, be identical to the active ingredient of naturally occurring GTF containing compositions. It is characterized by having the nitrogen of the pyridine ring, rather than the $R^7$ portion, coordinated to the chromium. It is readily synthesized and can be purified and stored for a reasonable length of time before use. The composition of matter set forth above is useful for the treatment of diabetics. A very useful aspect of the invention is that endogenous insulin becomes more active in the presence of such a composition of matter.

BEST MODE FOR CARRYING OUT INVENTION

The carbon atom content of various hydrocarbon-containing moieties is indicated by a prefix designating the minimum and maximum number of carbon atoms in the moiety, i.e., the prefix ($C_i$-$C_j$) indicates a moiety of the integer "i" to the interger "j" carbon atoms, inclusive. Thus ($C_1$-$C_4$) alkyl refers to alkyl of 1 to 4 carbon atoms, inclusive, or methyl, ethyl, propyl, cyclopropyl, isopropyl, n-butyl, s-butyl, t-butyl, cyclobutyl, 1-methylcyclopropyl, 2-methylcyclopropyl and cyclopropylmethyl.

In accordance with the present invention a composition of matter with the formula I above has been synthesized. Each of the groups $R^1$, $R^2$, $R^3$ and $R^4$ is preferably hydrogen or methyl, and is more preferably hydrogen. The group X, when present, is preferably OY and the group Y is generally hydrogen, a $C_{1-4}$ alkyl, and alkali metal ion, or an ammonium ion. The formula I set forth above is meant to include the salts and the anions formed by ionization, when applicable, of the pyridine derivative or of the salt.

Without being bound by theory, it is believed that if thiol groups are available on the potentiator such groups facilitate binding between insulin and its receptor. Thus, the preferred compounds described herein for the purpose of alleviating insulin resistance related diseases are believed to covalently bind, via a thiol disulfide-exchange reaction, with insulin and the thus formed potentiator-insulin compounds are believed to then, in turn, covalently bind to disulfides on the insulin receptor via a similar thiol/disulfide exchange mechanism.

The term "amino acid" as used herein means an organic acid containing both a basic amino group ($NH_2$) and an acidic carboxyl group (COOH); thus they are amphoteric and exist in aqueous solution as dipolar ions. The term "peptide" as used herein includes any amide derived from two or more such amino acids by combination of the amino group of one acid with the carboxyl group of another. Peptides useful in the practice of the present invention will generally have no more than 6 amino acids. Useful amino acids for the purposes of this invention are the alpha-, beta- and gamma-amino acids. The naturally occurring amino acids that have been established as protein constituents are alpha-amino acids. Many other amino acids occur in the free state in plant or animal tissue. Naturally occurring amino acids are those which are synthesized in nature. Other (non-naturally occurring) amino acids can also be readily synthesized and are useful in the practice of the present invention. Examples of amino acids are: alanine, β-alanine, arginine, cystathionine, cystine, glycine, histidine, homoserine, isoleucine, lanthionine, leucine, lysine, methionine, norleucine, norvaline, ornithine, proline, sarcosine, serine, threonine, thyronine, tyrosine, valine, cysteine, homocysteine, tryptophan, α-aspartic acid, β-aspartic acid, asparagine, α-glutamic acid, β-glutamic acid, glutamine, anthranilic acid, hippuric acid, 3,5-dibromotyrosine, 3,5-diiodotyrosine, hydroxylysine, hydroxyproline, isoleucine, phenylalanine, and thyroxine. The amino acids useful in the present invention can optionally have (in addition to those normally occurring in some of such acids) one or more of the substituents SH, $NH_2$, OH, COOH, $CH_2OH$, $OCH_3$, $OC_2H_5$, $SCH_3$, $SC_2H_5$, NH, Cl, Br, F, CCH or CN.

The group R of the compound $CRR^2(NR_2^1)COOH$ is usually selected from the group H, $CH_3$, $C_2H_5$, $CH(CH_3)_2$, $CH_2CH(CH_3)_2$, $C(CH_3)CH_2CH_3$, $CH_2CH_2CONH_2$, $CH_2CONH_2$, $CH_2OH$, $CH(CH_3)OH$, $CH_2SH$, $CH_2CH_2SCH_3$, $CH_2COOH$, $CH_2CH_2COOH$, $CH_2(CH_2)_3NH_2$, $CH_2(CH_2)_2NHC(NH)NH_2$, or $CR^5_2CR^5_2CONR^5CR^5(CR^5_2SH)CONR^5CR^5_2COOH$, wherein each $R^5$ is independently selected from hydrogen, $C_{1-4}$ alkyl, $C_{2-4}$ alkenyl and $C_{2-4}$ alkynyl. The compound $CRR^2(NR_2^1)COOH$ is preferably glutathione wherein $R^1$, $R^2$ and each $R^5$ (of the group R) is hydrogen.

Representative compounds of the formula I are shown below. Such compounds include but are not restricted to:

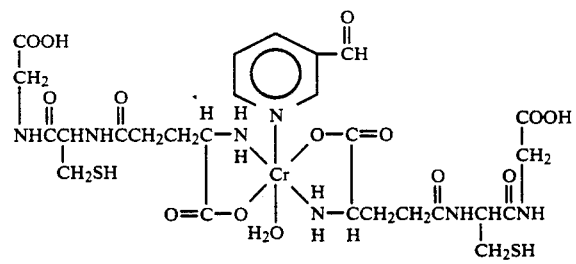

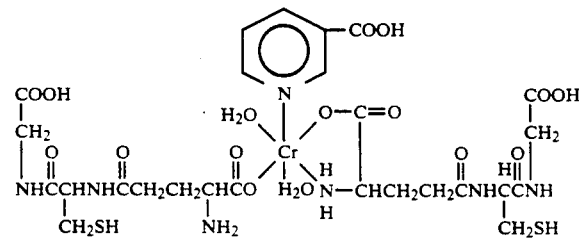

-continued
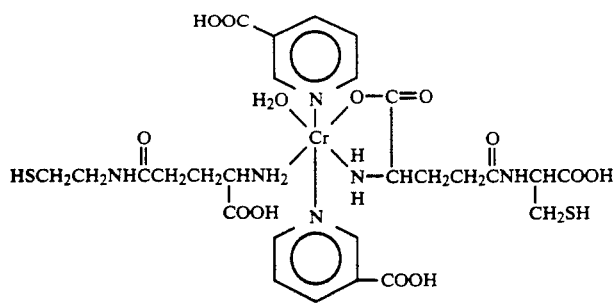
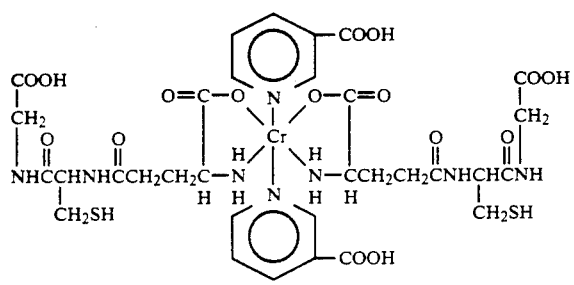
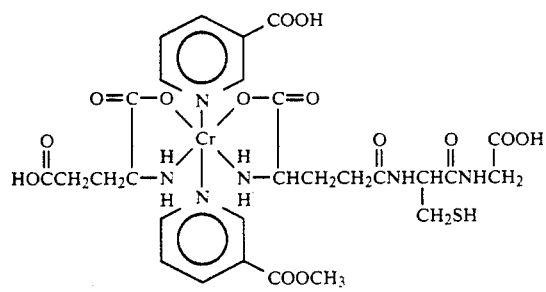
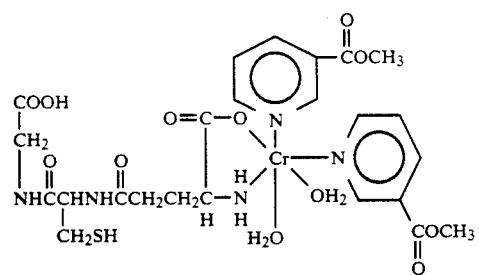
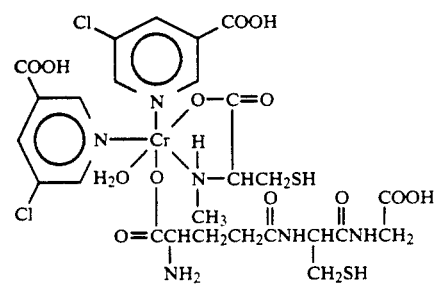

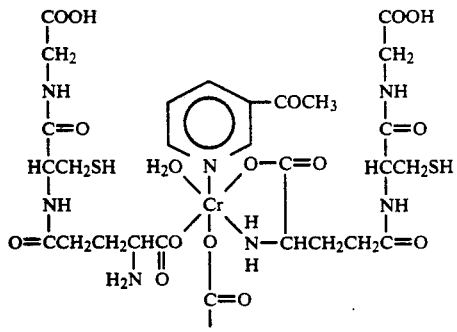

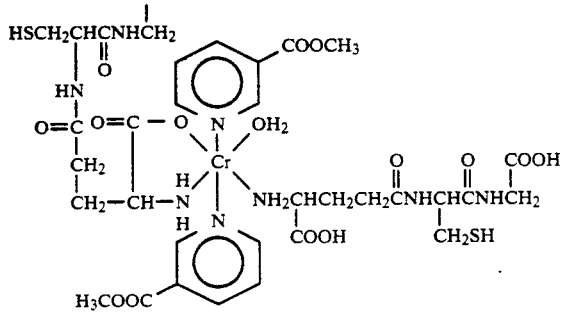

-continued

The compounds of the present invention may be oligomers. They may also be monomers. When the compounds are oligomers they are associated by bridging of the group $R^7$ or of the COO group of the substituent subscripted by "p" with another Cr(III).

The compounds of the invention are characterized by the chromium being in the Cr(III) state and being of octahedral symmetry. They are also most importantly and essentially characterized by having the nitrogen, rather than the $R^7$ portion, of the pyridine derivative ring coordinated to the Cr(III).

The oral route is preferred for administration of the potentiators. However, other systemic and non-systemic routes of administration may also be employed as long as the dosage used achieves the same blood level of drug or equivalent effect as the oral route. It may also be added in a mixture with or in association with insulin. The dosage regimen for the potentiator in accordance with this treatment will depend upon a variety of factors, including the type, age, weight, sex, and medical condition of the patient, the nature and dosage regimen of any insulin being administered to the patient and the particular potentiator to be administered.

In accordance with the method of the present invention a mixture of compounds of the formula I is synthesized. To carry out the synthesis by one method, a Cr(II) solution and a solution of $CRR^2(NR_2^1)COOH$ are mixed together in a reaction chamber under a non-oxidizing atmosphere. It is important that oxygen and any other oxidizing materials be excluded from the Cr(II) solution and from the solution of $CRR^2 (NR_2^1)$ COOH prior to the mixing, as well. This results in formation of a first reaction mixture. The first reaction mixture is maintained at a pH of about 4 to about 7, preferably about 5 to about 7, for a period of time sufficient for the Cr(II) and $CRR^2 (NR_2^1)$ COOH to react and form a first compound which, in the case where $CRR^2 (NR_2^1)$ COOH is glutathione, is a purple gelatinous precipitate. This precipitate occurs at certain high concentrations when a Cr(II) solution is added to a glutathione solution.

An alternate procedure is to add glutathione to a dilute Cr(II) solution. In this instance no precipitate is formed. This latter order of addition may be preferred if it is desirable to minimize the formation of polynuclear complexes involving chromium, i.e., monomers vs polymers or oligomers.

Reaction time may vary considerably but it is generally sufficient to leave the reactants together for from about 30 minutes to about 60 minutes. This is sufficient time for the purple gelatinous precipitate, if formed, to dissolve. The first reaction mixture can be maintained in the required pH range for a longer period of time but there is no advantage in doing so.

The temperature of the reaction is suitably in the range from about $-5°$ C. to about 60° C., for convenience at about 4° C. as controlled by an ice-water bath.

The pH of the solution is generally determined by the amount of the $CRR^2$ ($NR_2^1$) COOH solution added. Generally, the $CRR^2$ ($NR_2^1$) COOH solution can be made by dissolving $CRR^2$ ($NR_2^1$) COOH in deionized water under a stream of nitrogen gas and with the addition of alkali metal, e.g., sodium, hydroxide to adjust the pH to a desired value. The pH of the mixture is preferably held between about 5.5 and 7.5, more preferably in the range from about 5.9 to about 6.5, and still more preferably at approximately 6.0±0.1.

The Cr(II) solution can be made by dissolving high purity chromium metal under an inert atmosphere in the required amount of concentrated hydrochloric acid and deionized water. The solution can be stored under an inert atmosphere, for example nitrogen gas, and when not in use can be kept at a relatively low temperature, of the order of 4° C. This can be done to assure that the Cr(II) is not oxidized to Cr(III) or that, at least, such oxidation is minimized. Perchloric acid can be used in place of hydrochloric acid. The preparation is carried out in such a way that a small amount of chromium metal remains in contact with the solution; this assists in minimizing the oxidation of Cr(II) to Cr(III) in the stock solution.

The CRR$^2$ (NR$_2$$^1$) COOH is generally in an excess over the Cr(II). In general, the CRR$^2$ (NR$_2$$^1$) COOH will be in a molar ratio to the Cr(II) of at least about 5 to 1, more preferably about 10 to 1 and still more preferably about 20 to 1. Higher or lower molar ratios can be used; yields are influenced.

The compound

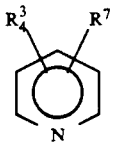

is added to the reacted first reaction mixture under a non-oxidizing atmosphere to form a second reaction mixture, wherein R$^4$ and R$^7$ are as previously defined.

The second reaction mixture is held under the non-oxidizing atmosphere for a time, usually 60 minutes, sufficient for the

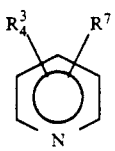

to react with the first compound and form the composition of matter of formula I. The solution of the compound

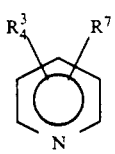

can be made by dissolving it in deionized water under a stream of nitrogen gas and with the addition of, for example, an alkali metal hydroxide such as sodium hydroxide, to adjust the pH. Generally an amount of the compound

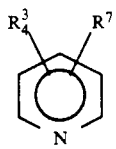

will be utilized which is in at least about a 5 to 1 molar ratio to the Cr(II), preferably at least about a 10 to 1 molar ratio.

The holding time can vary considerably, but a time of from about 30 minutes to about 60 minutes works well. If the reaction mixture is held too long, e.g., for days, the final reaction product, namely the resulting Cr(III) compound of formula I, may decompose.

One may further react the resulting composition of matter to the form wherein the initial R$^7$ is converted to a different R$^7$ by a conventional chemical reaction.

It may be desirable, in some instances, to admit oxygen or another oxidizing agent to the reaction chamber following the holding step so as to oxidize any remaining any unoxidized Cr(II) to Cr(III). However, the great majority of the Cr(II) will have already been oxidized to Cr(III) with a concomitant reduction of the compound

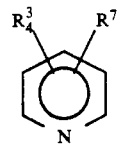

A composition of matter comprising a mixture of the formula I can be separated and purified from the second reaction by using gel permeation chromatography. It is preferable to carry out the chromatographic separation at relatively low temperature, below about 10° C., for example, at a convenient ice bath temperature of about 4° C. Generally, the chromatographic separation should be carried out utilizing an eluting solution which is buffered to a pH of approximately that of the reaction mixture. For example, a 0.1 molar phosphate ion buffer maintained at a pH of 6-8 may be utilized.

The invention also provides another method for synthesizing compounds of the formula I. In this synthesis method a Cr(II) solution is mixed together with a compound of the formula in a reaction chamber under a non-oxidizing atmosphere. It is important that oxygen and any other oxidizing materials be excluded from the Cr(II) solution and from the solution of the compound of the formula prior to the mixing, as well. This results in the formation of a first reaction mixture.

To the first reaction mixture a compound of the formula CRR$^2$ (NR$_2$$^1$) COOH was added and the mixture was stirred. The reaction can be carried out at any convenient temperature, for example any temperature from about 0° C. to about 100° C. When the compound of the formula CRR$^2$ (NR$_2$$^1$) COOH is glutathione it is convenient to carry out the reaction at a temperature of about 60° C. to facilitate its completion. When glutathione and nicotinic acid were used, all of the solid slurry of nicotinic acid with Cr(II) dissolved to form a clear red solution.

The pH for the reaction can be held at from about 4 to about 7, with the preferred pH being approximately 5. It may be desirable to add a basic solution, for example an alkali metal hydroxide solution such as sodium hydroxide, so as to maintain the pH at the desired value as the chromium solution is added to the solution of the compound of the formula

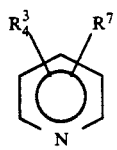

During the addition of the compound of the formula $CRR^2(NR_2^1)COOH$ the pH is preferably kept in the range from about 4 to about 7, and is most preferably kept at about 6. This pH is established by the pH of the $CRR^2(NR_2^1)COOH$ solution.

In yet another method the Cr(II), $CRR^2(NR_2^1)COOH$ and solutions are mixed together under a non-oxidizing atmosphere and are maintained at a pH of about 4 to about 7 at a temperature from about $-5°$ C. to about $60°$ C. for a sufficient time for a compound of formula I to form.

The composition of matter of the formula I is subject to slow decomposition and/or rearrangement. Such instability is not unexpected since Cr(III) thermodynamically prefers to be attached to acid groups such as carboxylic and the like as opposed to being attached to nitrogen.

The solution containing the composition of formula I can be frozen, for example at $-20°$ C., thereby greatly reducing the decomposition and/or rearrangement rate. Freeze drying techniques can be used to obtain solid material. Thus the compositions can be stored at low temperature for relatively long periods of time without seriously deteriorating. And, such temperatures are readily available in common refrigerators.

The invention will be better understood by reference to the following illustrative examples.

EXAMPLE I

Preparation of Purified Compounds of Formula I

A Cr(II) solution was made by dissolving 6.8 grams of metallic chromium under a nitrogen atmosphere with 21 ml of 12M HCl and 79 ml of deionized water. Oxygen was sparged from the liquids with nitrogen gas before the addition of chromium. The chromium was in pellet form and was added over a 10 minute period.

One and one-half ml of the Cr(II) solution was added to a solution of 12 g glutathione, a 20 to 1 molar ratio to the chromium, under a nitrogen atmosphere. The pH of the resulting reaction mixture was maintained at 6.0±0.1 by addition of deoxygenated sodium hydroxide and hydrochloric acid solutions, as needed. The reaction mixture was maintained at a temperature of 4° C. by the use of an ice-water mixture bath.

After about 30 minutes 1.9 g of nicotinic acid dissolved in 10 ml of sodium hydroxide solution (pH 6) and sparged to exclude oxygen, was added to the previous reaction mixture with sufficient nicotinic acid being added to provide a molar ratio thereof to chromium of 10 to 1. This required the addition of 10 ml of the nicotinic acid solution. The pH was adjusted to 6±0.1 by addition of deoxygenated sodium hydroxide and hydrochloric acid solutions, as needed. The temperature was maintained at about 4° C. with the use of an ice-water mixture bath. After about 60 minutes the reaction to form the desired product was substantially complete.

EXAMPLE II

Separation Of Purified Compounds of Formula I From Reaction Mixture Of Example I A column having dimensions of 2.5 cm diameter and 100 cm long and equipped with a surrounding jacket to permit cooling was filled with a gel size exclusion medium, Biogel P-2, having the capability of separating materials in the range of 100-1800 Daltons. In such gel filtrations the smaller fractions penetrate the interstices of the gel particles, thereby permitting the larger components to appear first at the exit end of the column.

A sample of the completed reaction mixture of Example I was applied to the top of the column and adsorbed and was followed with a solution of a 0.1 molar phosphate ion buffer, maintained at a pH of 6-8. This was performed with the column cooled to 4° C. This buffer solution was used to maintain a liquid flow and to force the sample through the column.

In some cases the ligands were more lipophilic (e.g., esters); in such cases the crude mixture was extracted with acetonitrile or chloroform and the aqueous phase was subjected to gel filtration chromatography.

Further separation was achieved by using a combination of reversed phase and ion exchange chromatography. For small amounts solid phase extraction (SPE) was used. Typically, the gel fraction was brought to pH 1.5 and passed through a $C_4$ SPE column. Some colored species (complexes) bound to the $C_4$ and some do not. The bound complexes were washed with 0.1M HCl/KCl pH 2 buffer and finally eluted with methanol and eventually the remaining complexes were eluted with a 1:1 mixture of 0.1M pH 7 phosphate buffer and methanol.

The $C_4$ non-bound material and the washings (pH 2 buffer) were adsorbed on $C_{18}$ SPE bonded phase, washed with 0.1M pH 2 buffer for the removal of any adsorbed free glutathione and nicotinic acid and the remaining complexes eluted partially with methanol and partially with the 1:1 mixture of 0.1M pH 7 phosphate buffer and methanol. Typically, the sample at pH 7 was diluted and loaded on a strong anionic resin medium (quaternary amine, e.g., J. T. Baker). After washing with water, the complexes were eluted with different concentrations of phosphate buffer, KCl solutions at pH values of 6-7 were used sometimes. If there was any adsorbed complex material left on the column, 0.2M HCl/KCl pH 2 buffer was used for the complete elution.

The other approach to the ion exchange was to dilute the SPE generated fractions, bring the pH to 2 and to apply the sample on the strong cation exchange resin (usually phenylsulfonic acid, e.g., J. T. Baker). After washing with water, different concentrations (from 0.02M to 1M) of pH 2 HCl/KCl buffer were used for elution. Then, if necessary, 0.1M pH 7 phosphate buffer was used and finally 0.1M ammonium hydroxide for the complete elution of the colored compounds.

For samples that were subjected to biological testing the methanol was removed in vacuo.

HPLC separations showed that the first colored bands from gel filtration chromatography that appeared were free of unreacted glutathione and were also free of unreacted nicotinic acid. Typically, HPLC columns comprised of $C_{18}$ were used with solvent elution. The mobile phase, usually water and methanol, employed the addition of ion-pairing reagents when appropriate.

The mobile phase typically included 97.4% water, 2.5% methanol and 0.1% trifluoroacetic acid as the ion pairing reagent.

The presence of glutathione or amino acid moieties was confirmed by the ninhydrin reaction. When SH was present its presence was confirmed and qualified spectrophotometrically using 6,6' dithiodinicotinic acid.

EXAMPLE III

Determination Of Composition Of Purified Compounds

In the preparation of reaction mixtures following the procedure of Example I solutions were used that had ratios of concentrations of glutathione and nicotinic acid to that of chromium of 20 and 10 to one, respectively. The use of such ratios served to drive the equilibrium reaction to essential completion; the ratios are not indicative of the true molar ratios in the actual compounds. To determine such molar ratios various purified compounds made in accordance with Example I were analyzed for chromium, —SH groups (a measure of glutathione) and nicotinic acid. The results are presented in the following Table 1 as molar ratios relative to chromium. It was found that in the chemical preparation step the ratio of glutathione to chromium influenced the final composition.

TABLE 1

Molar Composition Of Purified Complexes

| Sample No.* | Glutathione/Cr | Nicotinic acid/Cr |
|---|---|---|
| Chemical preparation-using glutathione to chromium ratio of twenty which gives a pink reaction mixture. | | |
| 84-1B | 1.0 | 1.5 |
| 86-2B | 1.0 | 0.94 |
| 96-2B | 1.2 | 1.0 |
| 100-1B | 1.4 | 1.2 |
| 109-2BP | 1.8 | 1.2 |
| 130-2BP | 1.6 | 1.1 |
| Average | 1.3 | 1.2 |
| Chemical preparation-using glutathione to chromium ratio of ten which gives a brown reaction mixture. | | |
| 73-1 | 0.63 | not measured |
| 74-3 | 0.84 | 1.4 |
| 79-2 | 0.73 | 1.7 |
| 80-1 | 0.67 | 1.4 |
| 81-3 | 0.88 | 1.6 |
| 82-1 | 0.62 | 1.7 |
| 83-1B | 0.62 | 0.88 |
| 87-1B | 0.80 | 1.4 |
| Average | 0.72 | 1.4 |

Note: meaning of designations.
Example: 84-1B. 1B is the first gel fraction from run 84 and was colored brown (B). 109-2BP is the second gel fraction from run 109 and was colored brown-pink (BP).

The complete purification leading to a single complex has not yet been achieved; therefore, the measured ratios reflect the average of several different compounds of the formula I.

EXAMPLE IV

Preparation and Purification of Anderson, et al Material

Anderson, et al have previously described synthesis of a compound having GTF-like activity but which, as will be seen, is different than the compound of the present invention. The synthesis as described by Anderson (J. Agric. Food Chem., Vol. 26, 1219, 1978, 1219) and Toepfer (J. Agric. Food Chem. 25, 162–166, 1977) was followed as closely as possible.

A Cr(III) solution was made by dissolving 4 g. $Cr(OAc)_3 \cdot H_2O$ in 750 ml of 80% ethyl alcohol containing 2 ml of glacial acetic acid. Four grams of nicotinic acid were added and the pH was adjusted to 7 with $NH_4OH$. The solution was stirred during refluxing for 3 hours. The color changed from green to blue-purple. That quantity (10.6 g) of glutathione needed for a 2/1 molar ratio of glutathione to chromium was added. This was followed by 4 hours of continuous stirring and refluxing. The material was stirred overnight without being heated. Alcohol was removed in vacuo, the solution was filtered to remove insoluble material, the residue was washed with water, and filtrate and washing were combined and reduced in vacuo to 300 ml. This solution had a deep red color. Thirty-eight ml of the solution was passed through a 2 cm × 55 cm Dowex-50 (WX-8, hydrogen form) (Trademark of The Dow Company) column. The absorbed materials were eluted with 0.1N $NH_4OH$. This fraction will be referred to as partially purified (PP).

The partially purified material was further purified by solid phase extraction. The pH of the Dowex-50 eluate was lowered to 1.5-2 with 3M HCl and the colored materials were adsorbed on $C_{18}$ medium. After washing with 0.1M pH 2 buffer (HCl/KCl) the complexes were eluted with methanol. This eluate was adsorbed on a strong cation exchange medium (J. T. Baker Bonded Phase-aromatic sulfonic acid), washed with pH 2 buffer and water; it was finally eluted with 0.1M $NH_4OH$ to provide fully purified Anderson, et al, material (FP).

EXAMPLE V

Method of Testing of Compounds

Tests of GTF-like activity of compounds were carried out by the in vitro glucose transport test on isolated adipocytes technique. This method is reported in the article "In Vitro Insulin Resistance of Human Adipocytes Isolated from Subjects with Non-Insulin-dependent Diabetes Meilitus", in J. Clin. Inves., 72, 1246 (1983) by Kashiwagi, et al. In the cited work human cells were used instead of animal cells as was true in the present case. Its purpose is to measure the efficiency of glucose transport through the membranes of living cells. The glucose was labelled with $C^{14}$ and radiometric measurements were made. In the tests a number of materials were processed, namely, insulin, epidydimal fat cell from rats, buffers, the material being tested and the labelled glucose. A run was conducted as a control to determine the transport of glucose into the fat cells brought about by the insulin alone. The increase in the transport of glucose over the control is a measure of the effectiveness of the candidate potentiator; this increase is reported as the percent increase over the control.

EXAMPLE VI

Comparative Testing of Materials

A listing of test results as carried out in accordance with Example V is tabulated in the following Table 2. In the table the compound glutathione was used in forming each candidate potentiator except those noted. The pyridine derivative was nicotinic acid unless otherwise noted. All unspecified purification/separation procedures were gel filtration chromatography.

TABLE 2

INSULIN POTENTIATING ACTIVITY OF CANDIDATE POTENTIATORS[a]

| Sample No. and Test Date | Cr(III) concentration × $10^{-7}$ molar in glucose transport test | over (% plus) or under (% minus) "control" |
|---|---|---|
| 86-1B | 2100 | 18 |
| 86-5P | 2300 | 13 |
| 86-5P | 2.3 | 40 |
| 87-1B | 9 | 27 |
| 86-5P | 0.58 | 49 |
| 86-4P[b] | 3.7 | 13 |
| 85-1P[c] | 9.2 | 49 |
| PP (See Example IV) | 3.1 | 9 |
| PP (See Example IV) | 6.2 | 4 |
| FP (See Example IV) | 3.4 | −5 |
| 130 C18-MeOH/pH 7 | 9.1 | 8 |
| 130-2BP | 4.4 | 12 |
| 130-4P | 6.5 | 12 |
| 130-C18-MeOH/pH 7 | 4.6 | 28 |
| 130-C18-MeOH/pH 7 -C4-MeOH/pH 7 | 3.6 | 22 |
| 130-C18-MeOH/pH 7 -C4-C18-MeOH/pH 7 | 4.5 | 30 |
| 126-C18-SCX/pH 7[d] | 2 | 39 |
| 156-C18-MeOH/pH 7[c] | 110 | 27 |
| 156-C18-MeOH/pH 7[c] | 1.1 | 32 |
| 151-Sephadex QAE[e] | 4.2 | 4 |
| 135[f] | 8.4 | 4 |
| 171[g] | 4.5 | 10 |

[a] Insulin Concentration Equal To 1000 pico Molar
[b] freshly separated after 3 months frozen storage
[c] pyridine derivative was methyl nicotinate
[d] pyridine derivative was pyridine-3-carboxaldehyde
[e] malonic acid was used rather than glutathione
[f] S-methylglutathione was used rather than glutathione
[g] glutamic acid was used rather than glutathione Note: The explanation following some Sample Nos. relates to purification/separation procedures E.g., C18-MeOH/pH 7 identifies the use of a $C_{18}$ column with MeOH with the eluting liquid being 1:1 mixture of MeOH and 0.1 M pH 7 phosphate buffer (SCX = strong cation exchange resin).

From the results of the samples that were tested at different concentrations (86-5P and 156-C18-MeOH/pH 7) one can see a general trend in that more diluted samples exhibited higher insulin potentiating activity. This suggests that, at higher concentrations of samples, there was inhibition. By lowering the concentration of the sample the inhibition effect was reduced and a higher percentage of insulin was bound to true insulin potentiators) during the incubation period. Therefore, the glucose transport was enhanced. No efforts were made to determine the lowest concentration of chromium complexes that show a significant insulin potentiation.

The results of the bioassays are particularly relevant in that insulin-mediated transport of glucose in NIDDM subjects was 40% lower than controls (Kashiwagi, A., et al, J. CLIN. n INVEST. 22, p 1246–1254, 1983). Thus enhancing the levels of glucose transport to 40% or more could have a significant beneficial effect upon insulin resistant subjects by normalizing glucose utilization.

The fraction referred to in Example V as partially purified (PP) showed some biological activity when tested as described in Example V. It is known, however, that large concentrations of nicotinic acid tested identically bring about a similar effect as reported by Lee, et al Biochem. Biophs. Acta 49, 408–410, 1961. The partially purified fraction was shown to have a large excess of nicotinic acid as Dowex-50 does not give good separation of the complexes from nicotinic acid; this was confirmed by spectrophotometric analysis for nicotinic acid. When the fully purified material of Example IV was tested no activity was found. This is consistent with the nicotinic acid being responsible for the activity found in the partially purified material. It is interesting to note that nicotinic acid was shown by Anderson, et al to have no effect on the assay they used. However, in the tests used herein nicotinic acid, in the amounts tested herein, does give a positive effect.

EXAMPLE VII

Proof Of Cr-Pyridine Nitrogen Coordination In Composition Of The Invention

An article related to this subject is Green and Tong, J.A.C.S., Vol. 78, 4896 (1956).

The aspect of the structure on which this invention has the greatest impact is the chromium coordination to the pyridine derivative. The compound of the present invention is characterized in that it has chromium coordinated to the nitrogen atom of the pyridine derivative and not to the $R^7$ group. The evidence for this having been achieved is related to the variation in the U.V. absorption of pyridine derivatives in their different chemical forms.

For example, nicotinic acid in water solutions exhibits different absorption peaks in the region of 260 nm depending on its ionic forms which are controlled by pH. These forms are:

1. In the pH range of 7–10 nicotinic acid exists as a minus one anion.

2. At low pH (>2) nicotinic acid exists as a plus one cation, due to the protonation of the pyridine nitrogen.

The absorption spectrum of each shows some distinctive although small differences, i.e., of the order of 2–3 nm (low pH 260 nm, high pH 262 nm). The absorption peaks move to higher wavelengths with alkylation of the nitrogen or coordination with chromium (low pH 262 nm, high pH 264 nm). When one coordinates the pyridine derivative nitrogen with a chromium atom the structures are restricted to two, namely the carboxylic acid form and its anion (since the pyridine derivative nitrogen is blocked by the chromium).

In addition, Green and Tong have demonstrated that the molar absorption coefficient changes with pH changes. These authors attribute this to the protonation-deprotonation of the pyridine nitrogen. Thus, chromium bonded to the nitrogen of nicotinic acid should not show any pH dependence of the molar absorption coefficient. This theory was tested with the cis- and trans-complexes of chromium, malonic and nicotinic acids whose preparation was reported by Broderick and Legg (Inorg. Chem. 1985, 24, 3724–3725). This assay was carried out on the materials of the present invention. No significant changes in molar absorption coefficient were noted with a change in pH for the fully characterized chromium-malonic acid-nicotinic complexes or with the material of the present invention. This, together with the consistent shift of the peak towards higher wavelengths, demonstrates that the pyridine derivative nitrogen in the compound of formula (I) is coordinated to the chromium. This procedure has been used routinely in qualifying the purified complexes of the invention as chromium-nitrogen bonded.

Chemical Evidence In Support Of The Existence Of Chromium-Nitrogen Coordination

The following experiment was performed for the purpose of proving that chromium (II) preferentially does not coordinate to the oxygen of the nicotinic acid carboxylic group.

The compound N-methyl nicotinic acid, also known as Trigonelline, was used in a reaction with chromium (II) and glutathione. The resulting chromium-containing materials were processed chromatographically. The chromium-containing material was separated in this way from the excess and unreacted ligands. The final complex was examined spectrophotometrically and found not to contain any nicotinic acid derivative. Thus, when the nitrogen was blocked no bonding of the nicotinic acid to chromium occurred. This is considered conclusive evidence that the complex of the invention does not involve bonding through the oxygen but rather through the pyridine nitrogen.

EXAMPLE VIII

Proof Of Carboxylic Acid Group Coordination In Material of Example IV

The discussion under Example VII also applies to this Example.

The material of Example IV referred to as fully purified was examined at 260 nm as a function of pH. Its absorption spectrum was no different than that of free nicotinic acid. There was a large, approximately 40%, dependence of the molar absorption coefficient on pH thus demonstrating chromium to oxygen rather than chromium to nitrogen bonding. Also, the values at peak maxima were characteristic of free nicotinic acid at both low and high pH values. Therefore, the material of Example IV had no significant amount of chromium bonded to the pyridine nitrogen.

EXAMPLE IX

The Use Of Pyridine Derivatives Other Than Nicotinic Acid

To determine if there might be some advantages to alternate syntheses a number of experiments were carried out in accordance with the procedure of Example I but using other reactants. Criteria used to classify the outcome of an experiment were the percent oxidation of Cr(II) and the presence of a charge transfer peak in the 280 nm-340 nm region, an indicator of formation of a complex. The latter was taken as evidence of the formation of the chromium-pyridine nitrogen coordination and therefore the formation of a compound of formula I.

In the course of the work leading to this invention, a distinctive charge transfer peak was observed in the range of 280 nm-340 nm in addition to the pyridine derivative ligand absorption at 250 nm. This charge transfer peak was only observed when the pyridine derivative nitrogen was coordinated with chromium along with glutathione. Another requirement for this charge transfer peak was a carbonyl group at the 3-position of the pyridine ring. When glutamic acid was substituted for glutathione, in the complex, the 280 nm-340 nm charge transfer peak was still observed. However, replacing glutathione with glycine eliminated the 280 nm-340 nm charge transfer peak. These observations indicate that glutathione probably binds to the chromium, in formula I, at the glutamic acid end rather than at the glycine end.

The complex prepared by the Anderson, et al procedure did not show the 280 nm-340 nm charge transfer peak even though glutathione was part of the complex. This suggests that the nicotinic acid, in the Anderson, et al complex, was not nitrogen bound to chromium.

Table 3 summarizes the highlights of the experiments.

TABLE 3
OXIDATION OF Cr(II) AND PRESENCE OF CHARGE TRANSFER BAND

| Pyridine Derivative | Charge Transfer Band at | Percent Cr(II) Oxidized |
|---|---|---|
| nicotinic acid | 308 nm | 95–100 |
| methyl-nicotinate | 280 nm | 85 |
| pyridine-3-carboxaldehyde | 325 to 340 nm | 100 |
| 3-methyl pyridine | None | Little, if any |
| iso-nicotinic acid | None | 95 |
| N-methyl-nicotinic acid | None | 93 |
| 3-hydroxymethyl-pyridine | None | Little, if any |
| Nicotinamide | 325 nm | 91 |
| pyridine | None | Little, if any |

* None = none found. Measured only if above 200 nm.

As demonstrated above there are a number of reactants that can be used in place of nicotinic acid. F

EXAMPLE X

Alternate Synthesis A

The synthesis described in Example I involves the complexing of Cr(II) with glutathione followed by adding nicotinic acid which reacts to form a complex with Cr(II) and glutathione and subsequently oxidizes the Cr(II) to Cr(III).

An alternate synthetic path was also studied. It entailed preparing a slurry of the Cr(II) with nicotinic acid. The reaction product of Cr(II) and nicotinic acid is insoluble $Cr(II)(NIC)_2(H_2O)_4$ a material first prepared by Broderick, et al, Inorg. Chem., 1986, 25, 3372–3377. To this glutathione was added and the mixture stirred. To facilitate the completion of the reaction the temperature was raised to 60° C. Eventually all of the solid dissolved leaving a clear red solution. On analysis it was found that some of the preferred complex was formed and that the Cr(II) was oxidized to Cr(III).

A typical preparation involved the addition of 6.5 ml of a 1.3 molar solution of Cr(II) to 10 ml of a 1.6 molar solution of nicotinic acid, all at room temperature. The pH was held at 5; sodium hydroxide solution was added to achieve this as there was a reduction in pH as the chromium was added. The first precipitate was red which changed to green-yellow. The mixture was stirred for about one hour, filtered and the resultant precipitate washed with deionized water. This material, although comprised of Cr(II), was air stable.

Glutathione was added to the suspension of the solid as described in an earlier paragraph; a molar ratio to Cr(II) of 20 was found to be effective. Alternately, the washed solid was suspended in a solution of glutathione. In this case the presence of bicarbonate ion has been found to promote the reaction with glutathione.

Alternate Synthesis B

Earlier mention is made of the use of pyridine derivatives other than nicotinic acid to oxidize Cr(II). One of these is pyridine-3 carboxaldehyde which when added to a solution of Cr(II) oxidized without the needed presence of glutathione. This is an important feature as one can maximize the pyridine derivative content in this way and then add the glutathione to obtain a complex containing the aldehyde and glutathione. The use of bicarbonate ion facilitates this latter reaction. Such a complex has been shown to have biological activity when used as such in the adipocyte procedure. If nicotinic acid is desired in the complex the aldehyde in the complex can be oxidized. Typical preparations involved molar ratios of aldehyde to chromium of ten to one and of glutathione to chromium of ten to one.

Alternate Synthesis C

Another pyridine derivative that has been studied is the methyl ester of nicotinic acid commonly called methyl nicotinate. It was found that the reaction product of this material with Cr(II) was soluble. The synthesis using this concept involved adding a solution of the ester to a solution of Cr(II); there was little or no oxidation of the chromium but there was a complex formed. To this solution glutathione was added to form the final complex; oxidation of the Cr(II) also occurred and was essentially 100%. Molar ratios of the ester and glutathione to chromium of ten to one were typically used in the solutions. Room temperature and a pH of 6 were employed. If saponification of the ester to the nicotinic acid is desired this can be accomplished by passing the solution of the complex through a strong anion exchange resin column in the hydroxy form at room temperature.

EXAMPLE XI

Demonstration of Non-Involvement of Sulfur In The Binding Of Glutathione To Chromium(III) In Preparation Of Compounds Of The Invention A set of experiments was specifically designed to show whether or not a third group will coordinate to chromium under the conditions described for Example 1 of this invention. Cysteine was chosen for this study as it is the source of thiol in glutathione. Also, it was important to determine if the 280 nm-340 nm charge transfer peak was due, in part, to a Cr—S linkage.

When cysteine was used at a pH of 6, 50% of the Cr(II) was oxidized by the cysteine, and the remaining Cr(II) was oxidized by addition of nicotinic acid; no 280-340 nm peak was observed. The 450 nm and 585 nm peaks attributable to Cr—S were not observed.

When cysteine was used in a separate experiment, at a pH of 8, 100% of the Cr(II) was oxidized by the cysteine. The distinctive peaks, at 450 nm and 585 nm, attributed to Cr—S were observed. Treatment with acid shifted these peaks to 400 nm and 540 nm which are normally observed when Cr(II) is not bound to sulfur. The severing of the sulfur bond was reversed by returning to high pH; these reactions were unusually fast for Cr(III). No 280 nm-340 nm charge transfer peaks were observed.

When S-methylcysteine was used at a pH of 8, 100% oxidation of Cr(II) was observed. The complex showed no Cr—S peaks and no 280 nm-340 nm peaks before or after addition of nicotinic acid.

When glutathione was complexed with Cr(II), no measurable oxidation of the Cr(II) was observed until the appropriate pyridine derivative was added to the complex mixture. At this time, the 280 nm-340 nm charge transfer peak also appeared. At no time were the 450 nm and 585 nm peaks attributable to Cr—S observed. Replacing glutathione with S-methylglutathione gave identical results.

Clearly, there is no indication of a Cr—S linkage at the pH region of the invention (approx. pH of 6). In addition, it follows that the charge transfer peak in the region of 280 nm-340 nm was not due to a Cr—S linkage. In fact, the experiment with cysteine at a pH of 8, which had Cr—S linkage, showed no 280 nm-340 nm peak. It is curious, however, that cysteine is capable of oxidizing Cr(II) to Cr(III). At this time, no mechanism has been postulated for this oxidation.

Finally, an experiment was run at pH 6 involving a mixture of glycine, cysteine, and glutamic acid (the three amino acids comprising the tripeptide, glutathione) and Cr(II). No oxidation of Cr(II) occurred even though free cysteine was present. This reaction mixture behaved similar to glutathione or glutamic acid, in that complete oxidation of the Cr(II) occurred upon addition of nicotinic acid to the complex mixture. The charge transfer peak at 280 nm-340 nm was observed. Apparently, the glutamic acid complexes Cr(II) and protects it from the cysteine.

As will be apparent from the above experimental examples a composition of matter has been prepared which has high GTF-like activity and which has the structure shown in formula I. The examples also illustrate that the composition prepared by Anderson, et al, while it may have some GTF-like activity, is a different compound, structurally, than are the compounds of the present invention, namely, it is structurally different than the compounds of formula I. Furthermore, the composition of matter of formula I has been shown to have very high GTF-like activity whereby it is useful for administration to those suffering from insulin resistance disorders such as diabetes, particularly NIDDM and IDDM plus NIDDM diabetics, either alone or in combination with a suitable carrier material to thereby effectively treat the insulin resistance disorders of such patients. The compounds can be made in different dosage forms including oral forms.

Industrial Applicability

The composition of matter of the present invention is useful for the treatment of diabetes r and other insulin resistant disorders. Furthermore, it can be prepared in relatively pure form and in relatively high quantities.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A composition of matter having GTF activity comprising:

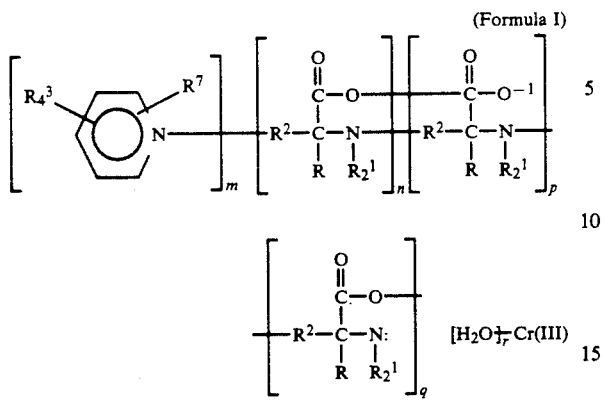

(Formula I)

the CR(III) having octahedral symmetry;

m=1, 2 or 3; n=0, 1 or 2; p=0, 1, 2, 3, 4 or 5; q=0, 1, 2, 3, 4 or 5; r=0, 1, 2 or 3;

$m+2n+p+q+r \leq 6$;

if p and q both=0, n=1 or 2;

if n=0, p and/or q≠0;

including mixtures and oligomers thereof, wherein each $R^1$ is independently selected from hydrogen, $C_{1-3}$ alkyl, $C_{2-3}$ alkenyl and $C_{2-3}$ alkynyl, or two $R^1$ form a ring having, including the N atom to which they are attached, 5 to 7 ring atoms;

each $R^2$ is independently selected from hydrogen, $C_{1-4}$ alkyl, $C_{2-4}$ alkenyl and $C_{2-4}$ alkynyl or two adjacent $R^1$ and $R^2$ form a ring having, including the N and C atoms to which they are attached, 5 to 7 ring atoms;

each $R^3$ is independently selected from hydrogen, fluoro, chloro, bromo, $C_{1-4}$ alkyl, $C_{2-4}$ alkenyl, $C_{2-4}$ alkynyl, COOH, $COOR^6$, CHO or $COR^6$, wherein $R^6$ is selected from $C_{1-4}$ alkyl, $C_{2-4}$ alkenyl and $C_{2-4}$ alkynyl or two adjacent $R^3$ form a ring having, including the atoms of the aromatic nitrogen containing ring to which they are attached, 5 to 7 ring atoms;

$R^7$ is CN or $CR_2^8OH$, $CR_2^8SH$, or $CR_2^8NH_2$, wherein each $R^8$ is independently H, $C_{1-4}$ alkyl, $C_{2-4}$ alkenyl or $C_{2-4}$ alkynyl, or COX, CSX or CNHX, wherein each X is independently H, $C_{1-4}$ alkyl, $C_{2-4}$ alkenyl, $C_{2-4}$ alkynyl, OY, $NR_2^4$ or SY, wherein Y is hydrogen, alkyl, an alkali metal or ammonium and each $R^4$ is independently selected from hydrogen, $C_{1-4}$ alkyl, $C_{2-4}$ alkenyl or $C_{2-4}$ alkynyl, or two geminal $R^4$ form a ring having, including the nitrogen atom to which they are attached, 5–7 ring atoms;

and each R is independently selected such that $R_2^1NCRR^2COOH$ is an amino acid or a peptide having no more than 6 amino acid residues, or such an amino acid or peptide having one or more of the substituents SH, $NH_2$, OH, COOH, $CH_2OH$, $OCH_3$, $OC_2H_5$, $SCH_3$, $SC_2H_5$, NH, Cl, Br, F, CCH or CN.

2. A method of synthesizing a pharmaceutically active composition of matter, comprising:

mixing together in a reaction chamber under a non-oxidizing atmosphere a Cr(II) solution and a solution of

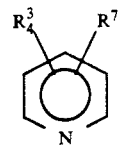

at a pH of about 4 to about 7 to form a first reaction mixture;

adding a solution of $CRR^2(NR_2^1)COOH$, to said first reaction mixture to form a second reaction mixture; and holding the second reaction mixture at a pH of about 4 to about 7 for a time sufficient for reaction to occur with the formation of the pharmaceutically active composition of matter;

wherein:

each $R^1$ is independently selected from hydrogen, $C_{1-3}$ alkyl, $C_{2-3}$ alkenyl and $C_{2-3}$ alkynyl, or two $R^1$ form a ring having, including the N atom to which they are attached, 5 to 7 ring atoms;

each $R^2$ is independently selected from hydrogen, $C_{1-4}$ alkyl, $C_{2-4}$ alkenyl and $C_{2-4}$ alkynyl or two adjacent $R^1$ and $R^2$ form a ring having, including the N and C atoms to which they are attached, 5 to 7 ring atoms;

each $R^3$ is independently selected from hydrogen, fluoro, chloro, bromo, $C_{1-4}$ alkyl, $C_{2-4}$ alkenyl, $C_{2-4}$ alkynyl, COOH, $COOR^6$, CHO or $COR^6$, wherein $R^6$ is selected from $C_{1-4}$ alkyl, $C_{2-4}$ alkenyl and $C_{2-4}$ alkynyl or two adjacent $R^3$ form a ring having, including the atoms of the aromatic nitrogen containing ring to which they are attached, 5 to 7 ring atoms;

$R^7$ is CN or $CR_2^8OH$, $CR_2^8SH$, or $CR_2^8NH_2$, wherein each $R^8$ is independently H, $C_{1-4}$ alkyl, $C_{2-4}$ alkenyl or $C_{2-4}$ alkynyl, or COX, CSX or CNHX, wherein each X is independently H, $C_{1-4}$ alkyl, $C_{2-4}$ alkenyl, $C_{2-4}$ alkynyl, OY, $NR_2^4$ or SY, wherein Y is hydrogen, alkyl, an alkali metal or ammonium and each $R^4$ is independently selected from hydrogen, $C_{1-4}$ alkyl, $C_{2-4}$ alkenyl or $C_{2-4}$ alkynyl, or two geminal $R^4$ form a ring having, including the nitrogen atom to which they are attached, 5–7 ring atoms;

and each R is independently selected such that $R_2^1NCRR^2COOH$ is an amino acid or a peptide having no more than 6 amino acid residues, or such an amino acid or peptide having one or more of the substituents SH, $NH_2$, OH, COOH, $CH_2OH$, $OCH_3$, $OC_2H_5$, $SCH_3$, $SC_2H_5$, NH, Cl, Br, F, CCH or CN. D 3. A method as set forth in claim 2, wherein the $CRR^2(NR_2^1)COOH$ and the

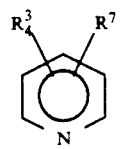

are each in a molar ratio of at least about 5:1 to the Cr(II).

4. A method as set forth in claim 3, wherein the molar ratio is at least about 10:1.

5. A method of synthesizing a pharmaceutically active composition of matter, comprising:

forming a solution in a reaction chamber under a non-oxidizing atmosphere of Cr(II), CRR$^2$(NR$_2^1$)COOH and

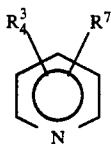

at a pH of about 4 to about 7 to form a reaction mixture; and holding said reaction mixture at a pH of about 4 to about 7 for a time sufficient for reaction to occur with the formation of the pharmaceutically active composition of matter;

wherein:

each R$^1$ is independently selected from hydrogen, C$_{1-3}$ alkyl, C$_{2-3}$ alkenyl and C$_{2-3}$ alkynyl, or two R$^1$ form a ring having, including the N atom to which they are attached, 5 to 7 ring atoms;

each R$^2$ is independently selected from hydrogen, C$_{1-4}$ alkyl, C$_{2-4}$ alkenyl and C$_{2-4}$ alkynyl or two adjacent R$^1$ and R$^2$ form a ring having, including the N and C atoms to which they are attached, 5 to 7 ring atoms; each R$^3$ is independently selected from hydrogen, fluoro, chloro, bromo, C$_{1-4}$ alkyl, C$_{2-4}$ alkenyl, C$_{2-4}$ alkynyl, COOH, COOR$^6$, CHO or COR$^6$, wherein R$^6$ is selected from C$_{1-4}$ alkyl, C$_{2-4}$ alkenyl and C$_{2-4}$ alkynyl or two adjacent R$^3$ form a ring having, including the atoms of the aromatic nitrogen containing ring to which they are attached, 5 to 7 ring atoms;

R$^7$ is CN or CR$_2^8$OH, CR$_2^8$SH, or CR$_2^8$NH$_2$, wherein each R$^8$ is independently H, C$_{1-4}$ alkyl, C$_{2-4}$ alkenyl or C$_{2-4}$ alkynyl, or COX, CSX or CNHX, wherein each X is independently H, C$_{1-4}$ alkyl, C$_{2-4}$ alkenyl, C$_{2-4}$ alkynyl, OY, NR$_2^4$ or SY, wherein Y is hydrogen, alkyl, an alkali metal or ammonium and each R$^4$ is independently selected from hydrogen, C$_{1-4}$ alkyl, C$_{2-4}$ alkenyl or C$_{2-4}$ alkynyl, or two geminal R$^4$ form a ring having, including the nitrogen atom to which they are attached, 5-7 ring atoms;

and each R is independently selected such that R$_2^1$NCRR$^2$COOH is an amino acid or a peptide having no more than 6 amino acid residues, or such an amino acid or peptide having one or more of the substituents SH, NH$_2$, OH, COOH, CH$_2$OH, OCH$_3$, OC$_2$H$_5$, SCH$_3$, SC$_2$H$_5$, NH, Cl, Br, F, CCH or CN.

6. A method as set forth in claim 5, wherein the CRR$^2$(NR$_2^1$)COOH and the

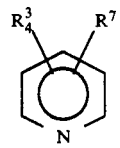

are each in a molar ratio of at least about 5:1 to the Cr(II).

7. A method as set forth in claim 6, wherein the molar ratio is at least about 10:1.

8. A method of treating a patient having an insulin resistance disease comprising administering to such patient a pharmacologically effective dosage of a composition of matter as set forth in claim 1.

9. A method as set forth in claim 8, wherein said disease comprises IDDM.

10. A method of treating a chromium deficient patient comprising administering to such patient a pharmacologically effective dosage of a composition of matter as set forth in claim 1.

* * * * *